United States Patent [19]

Li

[11] Patent Number: 4,754,758

[45] Date of Patent: Jul. 5, 1988

[54] SURGICAL CLOSURE DEVICE

[75] Inventor: Lehmann K. Li, Fairfield, Conn.

[73] Assignee: American Cyanamid Company, Stamford, Conn.

[21] Appl. No.: 851,761

[22] Filed: Apr. 14, 1986

[51] Int. Cl.[4] ............................................. A61B 17/04
[52] U.S. Cl. .................................. 128/334 C; 128/335
[58] Field of Search .................... 128/329, 330, 334 R, 128/334 C; 24/153.1, 150 FP, 111, 93, 155 R

[56] References Cited

U.S. PATENT DOCUMENTS

| 3,080,564 | 3/1963 | Strekopitor et al. | 227/19 |
|---|---|---|---|
| 3,252,643 | 5/1966 | Strekopytor et al. | 128/334 |
| 3,315,863 | 4/1967 | O'dea | 227/19 |
| 3,541,591 | 11/1970 | Hoegerman | 128/335 |
| 3,795,634 | 3/1974 | Strekopytor et al. | 227/19 |
| 4,060,089 | 11/1977 | Noiles | 128/334 C |
| 4,198,982 | 4/1980 | Fortner et al. | 228/334 C |
| 4,354,628 | 10/1982 | Green | 227/19 |
| 4,402,445 | 9/1983 | Green | 227/19 |
| 4,442,964 | 4/1984 | Becht | 227/19 |
| 4,513,746 | 4/1985 | Aranyi et al. | 128/334 C |
| 4,589,416 | 5/1986 | Green | 128/334 C |

FOREIGN PATENT DOCUMENTS

| 103707 | 4/1938 | Australia | 24/93 |
|---|---|---|---|
| 25123 | 5/1907 | United Kingdom | 24/93 |

Primary Examiner—Richard C. Pinkham
Assistant Examiner—Gary Jackson
Attorney, Agent, or Firm—David A. Warmbold; Charles F. Costello, Jr.

[57] ABSTRACT

A surgical closure device having two mating members is disclosed. The first member comprises a plurality of pins, an indentation ajacent the proximal end of each pin, and at least one synthetic tissue compatible first fiber connecting the distal end of each adjacent pin. The second member comprises at least one synthetic tissue compatible second fiber having a plurality of knots essentially equal in number to the plurality of pins. A method of closing a wound of living tissue using the surgical closure device is also disclosed.

9 Claims, 3 Drawing Sheets

SURGICAL CLOSURE DEVICE

BACKGROUND AND SUMMARY OF THE INVENTION

This invention relates to a surgical closure device.

A two part surgical closure device has been invented. The first part comprises a plurality of pins, and a flexible first means for connecting the distal end of each adjacent pin. The second part comprises means for holding the proximal end of each pin and a flexible second means for connecting the proximal end of each adjacent pin. In one embodiment, the plurality of pins are essentially symmetrical. In another embodiment, each adjacent pin is essentially parallel. In yet another embodiment, the first and second connecting means are essentially identical.

In a specific mode of the two part surgical closure device of this invention, the first part comprises a plurality of pins and at least one tissue compatible first fiber connecting the distal end of each adjacent pin. The second part comprises means for holding the proximal end of each pin and at least one tissue compatible second fiber connecting the proximal end of each adjacent pin. In one embodiment of this specific mode, each adjacent pin is essentially parallel. In another embodiment, the device is manufactured from a synthetic bioabsorbable material. In yet another emobidment, the material is a polymer containing at least one glycolic acid ester linkage. In a specific embodiment, the polymer is a copolymer.

In still another embodiment of the above described specific mode, the device is manufactured from a synthetic nonabsorbable material selected from the group consisting of a poly($C_2$–$C_{10}$ alkylene terephthalate), poly($C_2$–$C_6$ alkylene), polyamide, polyurethane and polyether-ester block copolymer. Specific embodiments of this material consist of poly(ethylene terephthalate) or poly(butylene terephthalate) as the poly($C_2$–$C_{10}$ alkylene terephthalate), and polybutester as the polyether-ester block copolymer.

Yet another embodiment of the above specific mode consists of a portion of the first fiber embedded in each pin. In still another embodiment, at least one of the fibers is hollow. In a further embodiment, each pin is connected to each adjacent pin by a plurality of fibers formed into a strand. In a specific embodiment, the strand is a ribbon.

In another specific mode, a surgical closure device having two mating members has been invented. The first member comprises a plurality of pins, an identation adjacent the proximal end of each pin, and at least one synthetic tissue compatible first fiber. The fiber connects the distal end of each adjacent pin. The second member comprises at least one synthetic tissue compatible second fiber having a plurality of knots essentially equal in number to the plurality of pins. The inside of diameter of each knot is essentially equal to or slightly less than the diameter of each pin. Each knot is capable of being held by a separate indentation on the first member.

In one embodiment, a portion of the first fiber is embedded in the distal end of each pin. In another embodiment, the second fiber has a plurality of square knots. In a further embodiment, the material composition of the second fiber is essentially equal to the first fiber.

DESCRIPTION OF THE INVENTION

Figure 1:
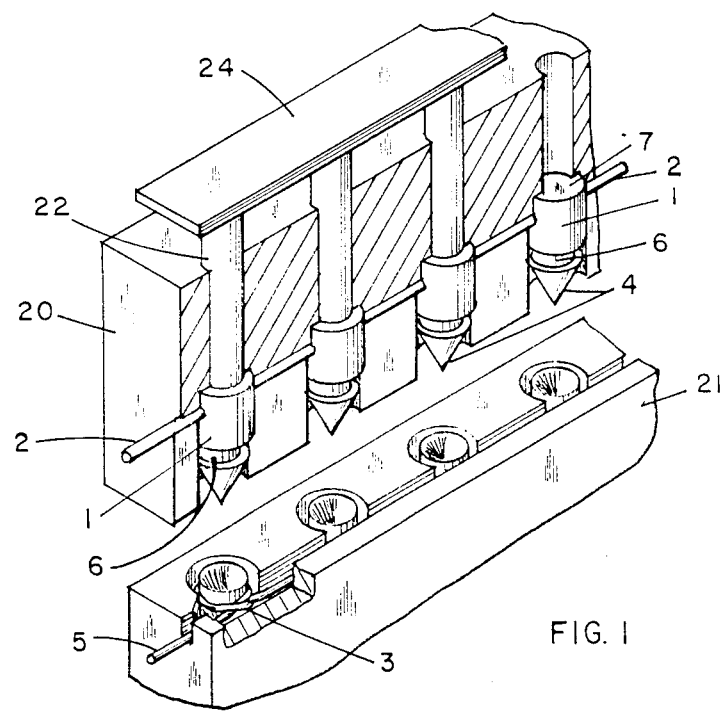
FIG. 1 is a partially cutaway perspective view showing the position of the surgical closure device in a mechanical applicator prior to use.
Figure 5:
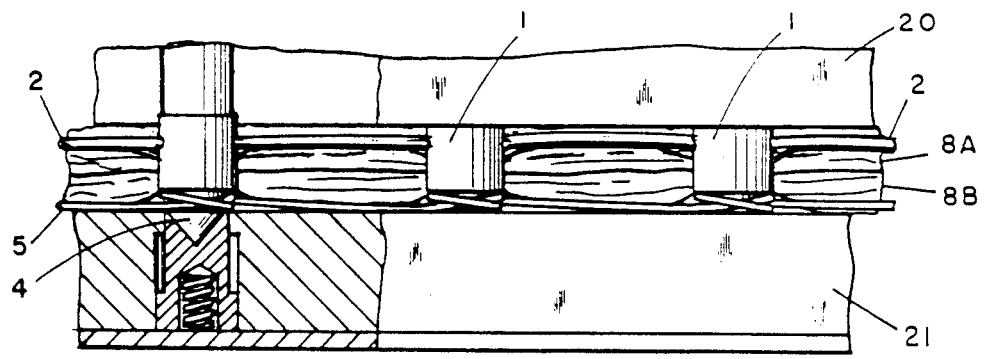
Figure 6:
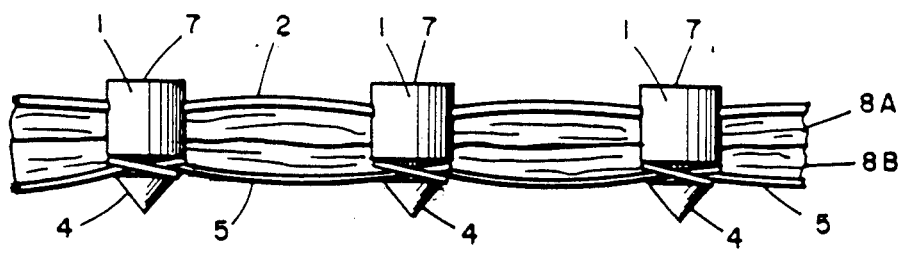
FIG. 6 is a front view of the closure device of FIG. 5 showing the approximation of living tissue.

Referring to FIG. 1, the first part of the surgical closure device comprises a plurality of pins 1. The plurality of pins 1 are essentially symmetrical. A flexible first means 2 for connecting each adjacent pin also comprises the first part. Prior to engagement with the first part, the second part comprises means 3 for holding the proximal end 4 of each first part pin 1. As shown in FIGS. 5 and 6 subsequent to engagement with the first part, the second part also comprises a flexible second means 5 for connecting the proximal ends 4 of each adjacent first part pin 1. The second connecting means 5 is integral with the holding means 3 prior and subsequent to engagement with the first part of the closure device.

Figure 2:
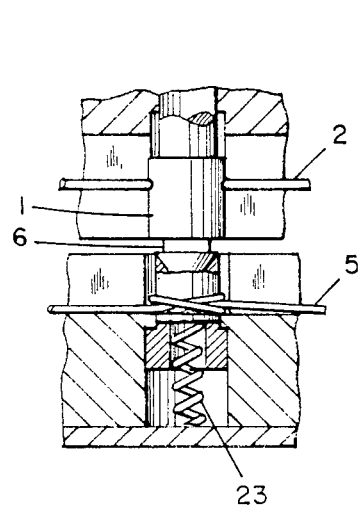
FIGS. 2 and 4 are partially cutaway front views showing the position of the closure device of FIG. 1 on partial activation of the mechanical applicator.
Figure 3:
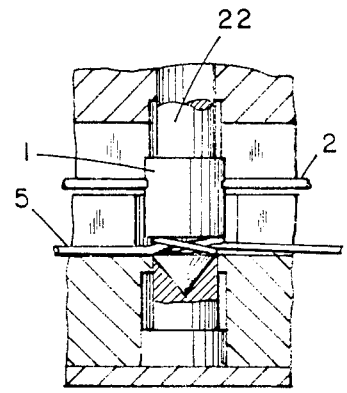
FIGS. 3 and 5 are partially cutaway front views showing the joining of the first and second closure device parts of FIG. 1 on complete activation of the applicator.
Figure 4:
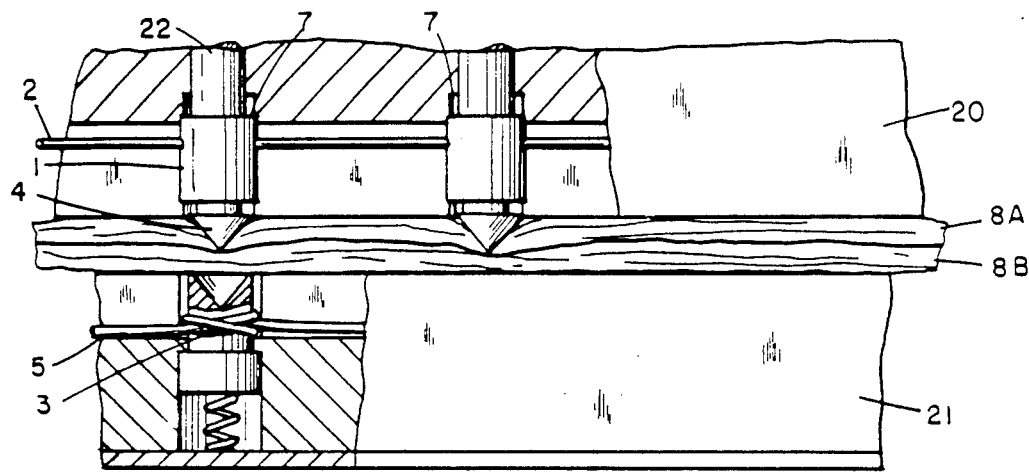

Referring to FIGS. 1, 2 and 4, the first and second connecting means 2 and 5, respectively, can be identical or different. The connecting means 2 and 5 can be a fiber or rod. The use of a fiber in one connecting means and a rod in the other connecting means is within the scope of this invention, provided that the fiber and rod are flexible. The use of a flexible fiber in both connecting means is preferred. The term fiber is used synonomously with the term connecting means 2 and 5 in conjunction with the FIGS. 1 to 6. This is because a flexible fiber is preferred. However, it is to be understood that a flexible fiber is only one specie of the generic term "connecting means", and therefore other species are encompassed within this term, for example, a rod, a braided strand such as a ribbon, and similar flexible materials.

Referring to FIGS. 2 to 5, at least one tissue compatible first fiber 2 connects each adjacent pin 1. The fiber 2 is adjacent to the distal end 7 of the pin 1. Referring specifically to FIG. 6, at least one tissue compatible second fiber 5 connects the proximal ends 4 of each adjacent pin.

Preferably, either one or both of the tissue compatible first and second fibers 2 and 5, respectively, are manufactured from a synthetic bioabsorbable material. The material can be a polymer containing at least one glycolic acid ester linkage. An example of a commercially available polymeric material is that contained in a surgical suture marketed under the trademark DEXON ® (American Cyanamid Company, Wayne, N.J., 07470 U.S.A.).

The polymer containing at least one glycolic acid ester linkage can be a copolymer. Examples of copolymers are those contained in the sutures marketed under the trademarks Vicryl ® (Ethicon, Inc., Sommerville, N.J., U.S.A.), and Maxon ® (American Cyanamid Company, Wayne, N.J. 07470, U.S.A.).

It is to be understood that the tissue compatible first and second fibers 2 and 5, respectively, can be, but it is not necessary that they are the same synthetic material. Further, it is to be understood that one or both of the tissue compatible fibers can be, but it is not necessary that they are bioabsorbable. For example, a nonabsorbable tissue compatible fiber can be used as both or either the first 2 and/or second 5 connecting means. An example of such a fiber is that contained in a suture manufactured by American Cyanamid Company, U.S.A. under the trademark Novafil ™.

Preferably, the first connecting means 2 shown for example in FIGS. 1 and 6 is permanently attached to pin 1 by any means for permanently attaching it. The attachment means can be, for example, by imbedding the fiber 2 in the plurality of pins 1. Alternatively, the pin 1 can be manufactured with a wedge, and the fiber 2 frictionally fit into the wedge, for example, as shown by analogy in U.S. Pat. No. 3,541,591 which is incorporated herein by reference. Other permanently attaching means can be, for example, by bonding. The bonding can be with an adhesive.

In using an adhesive, a hole can be drilled adjacent and perpendicular to the distal end of the pin 1. If the distal end is circular (as shown in FIG. 1), the hole is preferably drilled through the diameter. If the distal end is any other configuration, the hole is preferably drilled through the major axis. A portion of the fibre 2 is placed into the hole and then bonded to the pin, e.g. by an adhesive.

A semipermanent attaching means can also be used to connect the fiber 2 to the plurality of pins 1. Such a semipermanent attaching means can be, for example, an indentation adjacent to the distal end of the pin 1 (similar to the indentation 6 shown adjacent to the proximal end 4 of pin 1). The fiber 2, is then semipermanently attached to the indentation, such as by tying, for example with a square knot.

It is to be understood that the fibers 2 and/or 5 can be hollow, and can be of essentially any diameter, as long as the fibers remain flexible. Further, each connecting means 2 and 5 can be a plurality of fibers. The plurality of fibers can be braided, twisted, or combined by other knitting or weaving processes. In one embodiment, the braid can be a strand. The strand can be a ribbon.

Referring to FIGS. 1 and 4 to 6, the holding means 3 can comprise a plurality of knots. The number of knots are essentially equal to the number of pins 1. It is to be understood that the type of knot 3 on the fiber 5 is not critical to the practice of this invention provided that the knot 3 remains snug on the respective indentation 6. A square knot is useful in this regard.

Figure 7:
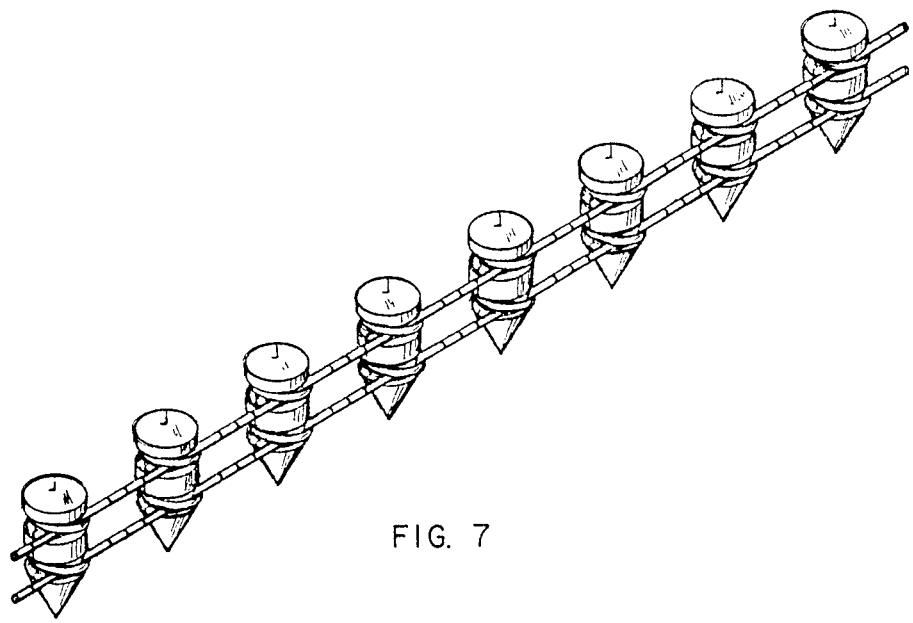
FIGS. 7 and 8 are perspective views showing the closure device in a parallel and circular configuration, respectively.
Figure 8:
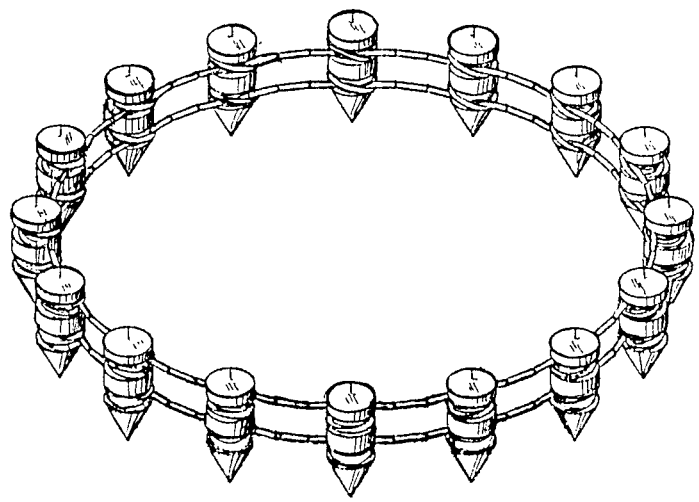

Referring to FIGS. 7 and 8, a parallel and circular configuration of the closure device is described. Many nontraumatic wounds tend to be in either of these two configurations. However, it is to be understood that various configurations of the closure device, for example sinusoidal, semicircular or curved, can be used, either alone or in combination with each other, or with a parallel or circular configuration.

A method of closing a wound with the surgical closure device of this invention has also been invented. Referring to FIGS. 4 to 6, the method comprises approximating the tissue 8. This approximation is done by placing the wound closure first part (which comprises the plurality of pins 1 and the connecting means 2) adjacent a tissue edge 8A, and the second part (which comprises the second connecting means 5) adjacent the other tissue edge 8B. Referring to FIG. 5, the tissue edges are approximated by compressing the first and/or second parts. While in this configuration, the knot 3 is compressed onto the indentation 6 of pin 1.

The wound closure device of this invention approximates living mammalian tissue, e.g. a tubular member during wound healing. The approximation with the closure device is done with a mechanical applicator. The type of mechanical applicator is not critical to the practice of this invention. That is, an applicator from the prior art can be adapted without undue experimentation to apply the wound closure device of this invention to a living mammalian tissue. The prior art applicators can apply the wound closure device in a straight or circular pattern, for example, as shown in FIGS. 7 and 8.

Examples of prior art applicators which can be adapted without undue experimentation included but are not limited to, a screw type, for example, an applicator having a wing nut, and a fulcrum type, for example an applicator having scissors-like or pliers-like handles.

Referring to FIGS. 1 to 3, the closure device first and second parts are contained in the applicator cooperating jaws 20 and 21, respectively. The means of containing the first and second closure device parts is not critical to the practice of this invention. For example, the pins 1 and the holding means 3 can be frictionally maintained in the respective jaws 20 and 21. The frictional force is less than the compressive force applied to either or both the plurality of rods 22 or spring 23.

The applicator, either a screw or fulcrum type, is activated by a compressive force. The means of activating are known in the prior art, e.g. as described in U.S. Pat. Nos. 4,513,746; 4,442,964; 4,402,445; 4,354,628; 4,198,982; 3,795,034; 3,275,211; and 3,252,643. Also see generally U.S. Pat. Nos. 3,315,863 and 3,080,564 which describe the same or a similar type applicator. All of these U.S. patents are incorporated herein by reference.

Referring to FIGS. 1 and 4 to 6, the activating means operates in a first mode on either or both of the jaws 20 and 21. After the first mode operation, the jaws 20 and 21 are placed in the position shown in FIG. 4. Referring to FIG. 1, the activating means then operates in a second mode on the plate 24. The plate 24 acts on the rods 22 to drive the pins 1 out of the cavities in the jaw 20. Continuous compression in the second mode sequentially allows the proximal end of the pin 4 to pierce the tissue 8A and 8B, to compress the spring 23, and to move the holding means 3 onto the indentation 6. This second mode is shown in FIGS. 4 and 5.

What is claimed:

1. A surgical closure device having two mating members, the first member comprising a plurality of pins, an indentation adjacent the proximal end of each pin, and at least one synthetic tissue compatible first fiber, said fiber connecting the distal end of each adjacent pin, and the second member comprising at least one synthetic tissue compatible second fiber having a plurality of knots essentially equal in number to said plurality of pins, the inside diameter of each knot being essentially equal to or slightly less than the diameter of each pin, whereby each knot is capable of being held by a separate indentation.

2. A device of claim 1 manufactured from a synthetic bioabsorbable material.

3. A device of claim 2 wherein said material is a polymer containing at least one glycolic acid ester linkage.

4. A device of claim 3 wherein said polymer is a copolymer.

5. A device of claim 1 manufactured from a synthetic nonabsorbable material selected from the group consisting of a poly($C_2$–$C_{10}$ alkylene terephthalate), poly($C_2$–$C_6$ alkylene), polyamide, polyurethane and polyester-ester block copolymer.

6. A device of claim 5 consisting of poly(ethylene terephthalate) or poly(butylene terephthalate) as the poly($C_2$–$C_{10}$ alkylene terephthalate), and polybutester as the polyether-ester block copolymer.

7. A device of claim 1 wherein a portion of said first fiber is embedded in the distal end of each pin.

8. A device of claim 7 wherein said second fiber has a plurality of square knots.

9. A device of claim 8 wherein the material composition of said second fibre is essentially equal to said first fiber.

* * * * *